US007176354B2

(12) United States Patent
Allen et al.

(10) Patent No.: US 7,176,354 B2
(45) Date of Patent: Feb. 13, 2007

(54) GENES ENCODING SULFATE ASSIMILATION PROTEINS

(75) Inventors: Stephen M. Allen, Wilmington, DE (US); Shawn L. Anderson, West Grove, PA (US); Mitchell C. Tarczynski, West Des Moines, IA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/829,432

(22) Filed: Apr. 21, 2004

(65) Prior Publication Data

US 2004/0177401 A1    Sep. 9, 2004

Related U.S. Application Data

(63) Continuation of application No. 09/720,384, filed as application No. PCT/US99/15809 on Jul. 13, 1999, now abandoned.

(60) Provisional application No. 60/092,833, filed on Jul. 14, 1998.

(51) Int. Cl.
 *A01H 1/00* (2006.01)
 *C07H 21/04* (2006.01)
 *C07K 14/415* (2006.01)
 *C12N 5/14* (2006.01)
 *C12N 9/00* (2006.01)

(52) U.S. Cl. .................. 800/295; 435/6; 435/69.1; 435/468; 435/419; 435/252.3; 435/320.1; 435/183; 530/370; 536/23.6; 800/278

(58) Field of Classification Search .................. 435/6, 435/69.1, 468, 419, 252.3, 320.1, 183; 530/370; 536/23.6; 800/278, 295
See application file for complete search history.

(56) References Cited

OTHER PUBLICATIONS

Frank W. Smith et al., PNAS, vol. 92:9373-9377, Sep. 1995, Plant Members of a Family of Sulfate Transporters Reveal Functional Subtypes.
Angelo Bolchi et al., Plant Mol. Biology, vol. 39:527-537, 1999, Coordinate Modulation of Maize Sulfate Permease and ATP Sulfurylase mRNAs in Response to Variations in Sulfur Nutritional Status: Stereospecific Down-Regulation by L-Cysteine.
Amit Setya et al., PNAS, vol. 93:13383-13388, Nov. 1996, Sulfate Reduction in Higher Plants: Molecular Evidence for a Novel 5'-adenylylsulfate Reductase.
Keiko Yonekura-Sakakibara et al., J. Biochem., vol. 124:615-621, 1998, Molecular Characterization of Tobaco Sulfite Reductase: Enzyme Purification, Gene Cloning, and Gene Expression Analysis.
Kazuki Saito et al., J. Biol. Chem., vol. 270(27):16321-16326, Jul. 7, 1995, Molecular Cloning and Characterization of a Plant Serine Acetyltransferase Playing a Regulatory Role in Cysteine Biosynthesis from Watermelon.
National Center for Biotechnology Information General Identifier No. 2832300, Aug. 10, 1998, Arz, H.E., A cDNA for Adenylyl Sulphate (APS)-kinase from *Arabidopsis thaliana*.
National Center for Biotechnology Information General Identifier No. 1076283, Dec. 7, 1999. Arz. H.E. et al., A cDNA for Adenylyl Sulphate (APS)-kinase from *Arabidopsis thaliana*.
Hildegard E. Arz et al., Biochimica et Biophysica Acta, vol. 1218:447-452, 1994, A cDNA for Adenylyl Sulphate (APS)-kinase from *Arabidopsis thaliana*.
Julie Ann Bick et al., Current Opinion in Plant biol., vol. 1(3):240-244, Jun. 1998, Plant Sulfur Metabolism—the Reduction of Sulfate to Sulfite.
Sandra Schiffmann et al., FEBS Letters, vol. 355:229-232, 1994, APS-Sulfotransferase Activity is Identical to Higher Plant APS-kinase.
Ajay Jain et al., Plant Phys., vol. 105:771-772, 1994, A cDNA Clone for 5'-Adenylylphosphosulfate Kinase from *Arabidopsis thaliana*.
Chen, Y et al., Plant Phys.-Suppl., vol. 108(2):72, Jun. 1995, Sulfate-Regulated Expression of ATP Sulfurylase and Adenosine-5-'-Phosphosulfate Kinase in *Brassica juncea*.
Sangman Lee et al., Biochem. and Biophys. Res. Comm., vol. 247:171-175, 1998, APS Kinase from *Arabidopsis thaliana*: Genomic Organization, Expression, and Kinetic Analysis of the Recombinant Enzyme.
Walbot, V., EMBL Accession No. AI637166, Apr. 27, 1999, Maize ESTs from Various cDNA Libraries Sequenced at Stanford University, XP002123195.
EMBL Sequence Library Data Accession No. D89631, Jul. 30, 1997, Sohlberg, L.E. et al., Nucleotide Sequence of cDNA encoding a Cys proteinase from germinating bean cotyledons, XP-002129910.
EMBL Sequence Library Data Accession No. O49307, Jun. 1, 1998, Federspiel, N.A. et al., XP-002129911.
EMBL Sequence Library Data Accession No. D25000, Nov. 30, 1993, Minobe, Y. et al., Rice cDNA from root, XP-002129912.
Frank W. Smith et al., PNAS, vol. 92:9373-9377, Sep. 1995, Plant members of a family of sulfate transporters reveal functional subtypes, XP-002129913.
Hideki Takahashi et al., Plant & Cell Phys., vol. 39 suppl, pp. S148, 1998, Antisense repression of sulfate transporter in transgenic *Arabidopsis thaliana* plants, XP-002121793.
Hideki Takahashi et al., PNAS, vol. 94:11102-11197, Sep. 1997, Regulation of sulfur assimilation in higher plants: A sulfate trnasporter induced in sulfate-starved roots plays a central role in *Arabidopsis thaliana*.
EMBL Sequence Library Data Accession No. X96761, Mar. 25, 1997, Ng. A. et al., Isolation & characterization of a lowly expressed cDNA from the resurrection grass *Sporobolus stapfianus* with homology to eukaryote sulfate transporter proteins, XP-002121791.
EMBL Sequence Library Data Accession No. AF016306, Jan. 8, 1998, Bolchi, A. et al., Coordinate modulation of maize sulfate permease and ATP sulfate permease and ATP sulfurylase mRNAs in response to variations in sulfur nutritional status: stereospecific down-regulation by L-cysteine, XP-002121790.

(Continued)

*Primary Examiner*—Phuong T. Bui

(57) ABSTRACT

This invention relates to an isolated nucleic acid fragment encoding a sulfate assimilation protein. The invention also relates to the construction of a chimeric gene encoding all or a portion of the sulfate assimilation protein, in sense or antisense orientation, wherein expression of the chimeric gene results in production of altered levels of the sulfate assimilation protein in a transformed host cell.

5 Claims, 2 Drawing Sheets

OTHER PUBLICATIONS

EMBL Sequence Library Data Accession No. O48889, Jun. 1, 1998, Bolchi, A. et al.

Frank W. Smith et al., The Plant Journal, vol. 12(4):875-884, 1997, Regulation of expression of a cDNA from barley roots encoding a high affinity sulphate transporter, XP-002129909.

Antje Prior et al., Biochimica et Biophysica Acta, vol. 1430:25-38, 1999, Structural and kinetic properties of adenylyl sulfate reductase from *Catharanthus roseus* cell cultures.

Senta Heiss et al., Plant Mol. Biol., vol. 39:847-857, 1999, Cloning sulfur assimlation genes of *Brassica juncea* L.: cadmium differentially affects the expression of a putative low-affinity sulfate transporter and isoforms of ATP sulfurylase and APS reductase.

John L. Wray et al., Chemico-Biological Interactions, vol. 109:153-167, 1998, Redefining reductive sulfate assimilation in higher plants: a role for APS reductase, a new member of the thioredoxin superfamily?.

Julie Ann Bick et al., Current Opinion in Plant Biology, 1998, pp. 240-244, Plant sulfur metabolism—the reduction of sulfate to sulfite.

Julie-Ann Bick et al., PNAS, vol. 95:8404-8409, Jul. 1998, Glutareodxin function for the carboxyl-terminal domain of the plant-type 5'-adenylylsulfate reductase.

Jose F. Gutierrez-Marcos et al, PNAS, vol. 93:13377-13382, 1996, Three members of a novel small gene-family from *Arabidopsis thaliana* able to complement funtionally an *Escherichia coli* mutant defective in PAPS reductase activity encode proteins with a thioredoxin-like domain and "APS reductase" activity.

Amit Setya et al., PNAS, vol. 93:13383-13388, 1996, Sulfate reduction in higher plants: Molecular evidence for a novel 5'-adenylylsulfate reductase.

EMBL Sequence Library Data Accession No. C27405, Aug. 6, 1997, Sasaki, T. et al., Rice cDNA from callus, XP-002121812.

EMBL Sequence Library Data Accession No. AF071890, Jun. 29, 1998, Mbeguie-A-Mbeguie D. et al., Molecular cloning and partial nucleotide sequence of a sulfite reductase from apricot fruit, XP-002128211.

EMBL Sequence Library Data Accession No. D50679, Dec. 1, 1997, Ideguchi, T. et al., cDNA cloning and functional expression of ferredoxin-dependent sulfite reductase from miaze in *E. coli* cells, XP-002128212.

Christine Bork et al., Gene, vol. 212:147-153, 1998, Isolation and characterization of a gene for assimiliatory sulfite reductase from *Arabidopsis thaliana*.

Andreas Bruhl et al., Biochimia et Biophysica Acta, vol. 1295:119-124, 1996, A cDNA clone from *Arabidopsis thaliana* encoding plastidic ferredoxin: sulfite reductase.

Database WPI, Derwent Publ., Ltd., JP-62 455773, Mitsubishi Corp., Sep. 6, 1994, XP-002121814.

EMBL Sequence Library Data Accession No. AU068082, Jun. 7, 1999, Sasaki, T. et al., Rice cDNA from callus, XP-002128630.

EMBL Sequence Library Data Accession No. AQ688702, Jul. 2, 1999, Yu, Y. et al., A BAC Encd sequencing framework to sequence the rice genome, XP-002128631.

Saito, K., Stress Responses of Photosynthetic organisms, 1998, pp. 215-226, Molecualr Aspects of Sulfur Assimilation and Acclimiation to Sulfur Supply in Plants.

Kazuki Saito et al., Plant Phys., vol. 106:887-895, 1994, Moedulation of Cystine Biosynthesis in Chloroplasts of Transgenic Tobacco Overexpressing Cystein Synthase [O-Acetylserine(thiol)-lyase]1.

Kazuki Saito et al., Comptes Rendu De L'Academie Des Sciences, vol. 319:969-973, 1996, Molecular characterization of cysteine biosynthetic enzymes in plants.

Yoo, B., et al., Plant Phys. suppl., vol. 114:267, 1997, Regulation of recombinant soybean serine acetyltransferase by CDPK.

EMBL Sequence Library Data Accession No. p93544, May 1, 1997, Saito, K. et al., XP-002128628.

EMBL Sequence Library Data Accession No. C26373, Aug. 6, 1997, Sasaki, T. Rice cDNA from callus, XP-002128627.

Michael A. Roberts et al., Plant Molecular biology, vol. 30:1041-1049, 1996, Cloning and characterisation of an *Arabidopsis thaliana* cDNa clone encoding an organellar isoform of serine acetyltransferase.

Kazuki Saito et al., Journ. of Biol. Chem., vol. 270(27):16321-16326, 1995, Molecular cloning and characterization of Plant Serine acetyltransferase playing a regulatory role in cystein biosynthesis from watermelon.

Deyrup, Andrea T. et al., "Deletion and Site-directed Mutagenesis of the ATP-binding Motif (P-loop) in the Bifunctional Murine Atp-Sulfurylase/Adenosine 5'-Phosphosulfate Kinase Enzyme," The Journal of Biological Chemistry, Apr. 17, 1998, pp. 9450-9456, vol. 273, No. 16.

Macrae, Ian J. et al., "Crystal Structure of Adenosine 5'-Phosphosulfate Kinase from *Penicillium chrysogenum*," Biochemistry, 2000, pp. 1613-1621, vol. 39.

Satishchandran, C. et al., "Characterization of the Phosphorylated Enzyme Intermediate Formed in the Adenosine 5'-Phosphosulfate Kinase Reaction," Biochemistry, 1992, pp. 11684-11688, vol. 31.

National Center for Biotechnology Information General Identifier No. 3529, Accession No. CAA46252, Apr. 18, 2005, A. Dusterhoft et al, DNA sequencing and analysis of a 14.7 kb segment encompassing centromere CEN11 of *Saccharomyces cerevisiae* reveals nine previously unknown open reading frames.

Figure 1A

```
                          1                                                           60
SEQ ID NO:2    ------------------------------------------------------------
SEQ ID NO:4    RPFHFINQTEPLVTHTQQPPSPAPGPASQ-GQRQGNTLLSPTPTLAVILVNPQRAPPVLP
SEQ ID NO:6    ------------------------------------------------------------
SEQ ID NO:8    ------------ARATAKALRQPCYAGIFRNIEC-GPSPAAESLGFPKLRG-----INV
SEQ ID NO:10   ---------------------------------------TRADAGERMA----------G
SEQ ID NO:12   T-----------------------------------------------------------
SEQ ID NO:13   ----------------MIGSVKRPVVSCVLPEFDFTESTGLGKKSSSVKLPVNFG----AFG
SEQ ID NO:14   -------------------MIAAGAKSLL-------------GLSMASPK----G----IFD 61                                                          120
SEQ ID NO:2    SAA--------------AAVAGISSSSSA---------------------------------
SEQ ID NO:4    GLTPSDAPLPALVIHGLTPRSSHSSAGLASDSGRREGEGRGARTHCHRGIGRWVRRRRRN
SEQ ID NO:6    TGLHCGRRGLVLVLRAKSKPIRAKEN--ASVSASLID-DWFKPITAKED----------S
SEQ ID NO:8    SEA-----------VPVVAVAAGKQP-----VNG--------------------------
SEQ ID NO:10   SGG--GEVKLGFLAPIKATEGSKTSS--FQVNGKVDNFRHLQPSDCNSN----------S
SEQ ID NO:12   SNSMSNSRSVVVVRACVSMDGSQTLS--HNKNGSIPEVKSI-------------------
SEQ ID NO:13
SEQ ID NO:14

121                                                         180
SEQ ID NO:2    ------------LVTSTVGKSTNILWHECAIGQKERQGLLNQKGCVWITGLSGSGK
SEQ ID NO:4    GAAPGEAPHSPVKEKPVMSNIGKSTNILWHNCLIGQSDRQKLLGQKGCVWITGLSGSGK
SEQ ID NO:6    ----------SIVPKASNIFWHDCAVGQADRQKLLKQKGCVWITGLSGSGK
SEQ ID NO:8    NAE-DRTSSFSGKNLTQMSNVGNSTNIMWHDCPIQKQDRQLLQQQGCVIWLTGLSGSGK
SEQ ID NO:10   -----SAMAGIDKLVTSTVGKSTNVLWHDCPIGQFERQELLNQKGCVWITGLSGSGK
SEQ ID NO:12   DSSLNNCNGFPGKKILQTTVGNSTNILWHKCAVEKSERQEPLQQRGCVIWITGLSGSGK
SEQ ID NO:13
SEQ ID NO:14   ------NGHTGQKQGPLSTVGNSTNIKWHECSVEKVDRQRLLDQKGCVIWVTGLSGSGK
```

Figure 1B

```
              181                                                       240
SEQ ID NO:2   STLACALSRELHGRGHLTYVLDGDNLRHGINRDLSFGAEDRAENIRRVGEVAKLFADAGL
SEQ ID NO:4   STLACALSRELHCRGHLTYVLDGDNLRHGLNRDLSFKAEDRAENIRRVGEVAKLFADAGV
SEQ ID NO:6   STLACTLDRELHTRGKLSYVLDGDNLRHGLNKDLGFKAEDRAENIRKVGEVAKLFXDASL
SEQ ID NO:8   STIACALSQSLHSKGKLSYILDGDNIRHGLNQDLSFRAEDRSENIRRIGEVAKLFADAGV
SEQ ID NO:10  STLACALSRELHSRGHLTYILDGDNLRHGLNRDLCFEAKDRAENIRRVGEVAKLFADAGL
SEQ ID NO:12  ------------------------------------------------------------
SEQ ID NO:13  STLACALSRGLHAKGKLTYILDGDNVRHGLNSDLSFKAEDRAENIRRIGEVAKLFADAGV
SEQ ID NO:14  STLACALNQMLYQKGKLCYILDGDNVRHGLNRDLSFKAEDRAENIRRVGEVAKLFADAGI 241                                                       300
SEQ ID NO:2   VCIASLISPYRSDRSACRDLLPKHSFIEVFLDVPLQVCEARDPKGLYKLARAGKIKGFTG
SEQ ID NO:4   ICIASLISPYRRDRDACRALLPHSNFIEVFIDLPLKICEARDPKGLYKLARTGKIKGFTG
SEQ ID NO:6   VCIASFKSPYKRER----------------------------------------------
SEQ ID NO:8   ICITSLISPYQKDRDACRALLSKGDFIEVFIDVPLHVCEARDPKGLYKLARAGKIKGFTG
SEQ ID NO:10  ICIASLISPYRSERSACRKLLHNSTFIEVFLNVPLEVCEARDPKGLYKLARAGKIKGFTG
SEQ ID NO:12  ------------------------------------------------RLARTGKIKGFTG
SEQ ID NO:13  ICIASLISPYRKPPDACRSLLPEGDFIEVFMDVPLKVCEARDPKGLYKLARAGKIKGFTG
SEQ ID NO:14  ICIASLISPYRTDRDACRSLLPEGDFVEVFMDVPLSVCEARDPKGLYKLARAGKIKGFTG 301                                            344
SEQ ID NO:2   IDDPYEPPSDCEIVIQCKVGDCPSPESMAGHVVSYLETNGFLQD
SEQ ID NO:4   IDDPYEPPINGEIVIKMKDEECPSPKAMAKQVLCYLEENGYLQA
SEQ ID NO:6   -------------------------------------------ES
SEQ ID NO:8   IDDPYEPPCSCEIVLQQKGSDCKSPSDMAEEVISYLEENGYLRA
SEQ ID NO:10  IDDPYEAPSDCEIVIQCKAGDCATPKSMADQVVSYLEANEFLQE
SEQ ID NO:12  VDDPYESPVNSEIVIKMEGGECPSPKAMAQQVLSYLEKNGYLQA
SEQ ID NO:13  IDDPYEPPLKSEIVLHQKLGMCDSPCDLADIVISYLEENGYLKA
SEQ ID NO:14  IDDPYEPPLNCEISLGREGG--TSPIEMAEKVVGYLDNKGYLQA
```

GENES ENCODING SULFATE ASSIMILATION PROTEINS

This application is a continuation of U.S. application Ser. No. 09/720,384, filed Dec. 21, 2000, now abandoned, which is a National Stage Application of PCT/US99/15809, filed Jul. 13, 1999, which claims the benefit of U.S. Provisional Application No. 60/092,833, filed Jul. 14, 1998.

FIELD OF THE INVENTION

This invention is in the field of plant molecular biology. More specifically, this invention pertains to nucleic acid fragments encoding sulfate assimilation proteins in plants and seeds.

BACKGROUND OF THE INVENTION

Sulfate assimilation is the process by which environmental sulfur is fixed into organic sulfur for use in cellular metabolism. The two major end products of this process are the essential amino acids cysteine and methionine. These amino acids are limiting in food and feed; they cannot be synthesized by animals and thus must be acquired from plant sources. Increasing the level of these amino acids in feed products is thus of major economic value. Key to that process is increasing the level of organic sulfur available for cysteine and methionine biosynthesis.

Multiple enzymes are involved in sulfur assimilation. These include: High affinity sulfate transporter and low affinity sulfate transporter proteins which serve to transport sulfur from the outside environment across the cell membrane into the cell (Smith et al. (1995) *PNAS* 92(20): 9373–9377). Once sulfur is in the cell sulfate adenylyltransferase (ATP sulfurylase) (Bolchia et al. (1999) *Plant Mol. Biol.* 39(3):527–537) catalyzes the first step in assimilation, converting the inorganic sulfur into an organic form, adenosine-5'phospho-sulfate (APS). Next, several enzymes further modify organic sulfur for use in the biosynthesis of cysteine and methionine. For example, adenylylsulfate kinase (APS kinase), catalyzes the conversion of APS to the biosynthetic intermediate PAPS (3'-phospho-adenosine-5' phosphosulfate) (Arz et al. (1994) *Biochim. Biophy. Acta* 1218(3): 447–452). APS reductase (5' adenylyl phosphosulphate reductase) is utilized in an alternative pathway, resulting in an inorganic but cellularly bound (bound to a carrier), form of sulfur (sulfite) (Setya et al. (1996) *PNAS* 93(23):13383–13388). Sulfite reductase further reduces the sulfite, still attached to the carrier, to sulfide and serine O-acetyltransferase converts serine to O-acetylserine, which will serve as the backbone to which the sulfide will be transferred to from the carrier to form cysteine (Yonelcura-Sakakibara et al. (1998) *J Biolchem.* 124(3):615–621 and Saito et al. (1995) *J. Biol. Chem.* 270(27):16321–16326).

As described, each of these enzymes is involved in sulfate assimilation and the pathway leading to cysteine biosynthesis, which in turn serves as an organic sulfur donor for multiple other pathways in the cell, including methionine biosynthesis. Together or singly these enzymes and the genes that encode them have utility in overcoming the sulfur limitations known to exist in crop plants. It may be possible to modulate the level of sulfur containing compounds in the cell, including the nutritionally critical amino acids cysteine and methionine. Specifically, their overexpression using tissue specific promoters will remove the enzyme in question as a possible limiting step, thus increasing the potential flux through the pathway to the essential amino acids. This will allow the engineering of plant tissues with increases levels of these amino acids, which now often must be added a supplements to animal feed.

SUMMARY OF THE INVENTION

The instant invention relates to isolated nucleic acid fragments encoding sulfate assimilation proteins. Specifically, this invention concerns an isolated nucleic acid fragment encoding an APS kinase and an isolated nucleic acid fragment that is substantially similar to an isolated nucleic acid fragment encoding an APS kinase. In addition, this invention relates to a nucleic acid fragment that is complementary to the nucleic acid fragment encoding APS kinase. An additional embodiment of the instant invention pertains to a polypeptide encoding all or a substantial portion of an APS kinase.

In another embodiment, the instant invention relates to a chimeric gene encoding an APS kinase, or to a chimeric gene that comprises a nucleic acid fragment that is complementary to a nucleic acid fragment encoding an APS kinase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an APS kinase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an APS kinase in a transformed host cell comprising: a) transforming a host cell with a chimeric gene comprising a nucleic acid fragment encoding an APS kinase; and b) growing the transformed host cell under conditions that are suitable for expression of the chimeric gene wherein expression of the chimeric gene results in production of altered levels of APS kinase in the transformed host cell.

An addition embodiment of the instant invention concerns a method for obtaining a nucleic acid fragment encoding all or a substantial portion of an amino acid sequence encoding an APS kinase.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIGS. 1A and 1B show a comparison of the amino acid sequences of the sequences set forth in SEQ ID NOs:2, 4, 6, 8, 10 and 12 and the *Catharanthus roseus* and *Arabidopsis thaliana* sequences (SEQ ID NOs:13 and 14 respectively).

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Sulfate Assimilation Proteins

| Protein | Clone Designation | SEQ ID NO: (Nucleotide) | (Amino Acid) |
|---|---|---|---|
| APS kinase | cen3n.pk0088.b10 | 1 | 2 |
| APS kinase | p0016.ctscj40rb | 3 | 4 |
| APS kinase | r10n.pk112.o11 | 5 | 6 |
| APS kinase | sdp2c.pk013.a11 | 7 | 8 |
| APS kinase | wr1.pk0101.e2 | 9 | 10 |
| APS kinase | wre1n.pk0069.g5 | 11 | 12 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool: Altschul et al. (1993) *J. Mol. Biol.* 216:403–410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "subatantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above. "Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences. "Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several sulfate assimilation proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other APS kinase enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides. can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of APS kinase in those cells. This enzyme is involved in sulfate assimilation and the pathway leading to cysteine biosynthesis, which in turn serves as an organic sulfur donor for multiple other pathways in the cell, including methionine biosynthesis. This enzyme and the gene(s) that encodes the protein has utility in overcoming the sulfur limitations known to exist in crop plants. It may be possible to modulate the level of sulfur containing compounds in the cell, including the nutritionally critical amino acids cysteine and methionine. Specifically, their overexpression using tissue specific promoters will remove the enzyme in question as a possible limiting step, thus increasing the potential flux through the pathway to the essential amino acids. This will allow the engineering of plant tissues with increases levels of these amino acids, which now often must be added a supplements to animal feed.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded sulfate assimilation protein. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Seguencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cen3n | Corn (*Zea mays* L.) endosperm stage 3 (20 days after pollination)* | cen3n.pk0088.b10 |
| p0016 | Corn (*Zea mays* L.) pooled tassel shoots 0.1–1.4 cm | p0016.ctscj40rb |

TABLE 2-continued cDNA Libraries from Corn, Rice, Soybean and Wheat

| Library | Tissue | Clone |
|---|---|---|
| r10n | Rice (*Oryza sativa* L.) 15 day leaf* | r10n.pk112.o11 |
| sdp2c | Soybean (*Glycine max* L.) developing pods 6–7 mm | sdp2c.pk013.a11 |
| wr1 | Wheat (*Triticum aestivum* L.) root; 7 day old seedling, light grown | wr1.pk0101.e2 |
| wre1n | Wheat (*Triticum aestivum* L.) root; 7 day old etiolated seedling* | wre1n.pk0069.g5 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP* XR vectors according to the manufacturer's protocol (Stratagene Cloning Systems, La Jolla, Calif.). The Uni-ZAP* XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding sulfate assimilation proteins were identified by conducting BLAST (Basic Local Alignment Search Tool; Altschul et al. (1993) *J. Mol. Biol.* 215: 403–410) searches for similarity to sequences contained in the BLAST "nr" database (comprising all non-redundant GenBank CDS translations, sequences derived from the 3-dimensional structure Brookhaven Protein Date Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding APS Kinase

The BLASTX search using the EST sequences from clones listed in Table 3 revealed similarity of the polypeptides encoded by the cDNAs to APS kinase from *Catharanthus roseus* (NCBI Identifier No. gi 2832300) and *Arabidopsis thaliana* (NCBI Identifier No. gi 1076283). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to *Catharanthus roseus* and *Arabidopsis thaliana* APS Kinase

| Clone | Status | BLAST pLog Score |
|---|---|---|
| cen3n.pk0088.b10 | EST | 88.30 (gi 2832300) |
| p0016.ctscj40rb | FIS | 88.50 (gi 2832300) |
| r10n.pk112.o11 | EST | 52.30 (gi 1076283) |
| sdp2c.pk013.a11 | FIS | 97.30 (gi 2832300) |
| wr1.pk0101.e2 | FIS | 84.50 (gi 2832300) |
| wre1n.pk0069.g5 | FIS | 14.30 (gi 2832300) |

FIGS. 1A and 1B present an alignment of the amino acid sequences set forth in SEQ ID NOs:2, 4, 6, 8, 10 and 12 and the *Catharanthus roseus* and *Arabidopsis thaliane* sequences (SEQ ID NOs:13 and 14 respectively). The data In Table 4 represents a calculation of the percent identity of the amino acid sequences set forth in SEQ ID NOs:2, 4, 6, 8, 10 and 12 and the *Catharenthus roseus* and *Arabidopsis thaliana* sequences (SEQ ID NOs:13 and 14).

TABLE 4

Percent Identity of Amino Acid Sequences Deduced From the Nucleotide Sequences of cDNA Clones Encoding Polypeptides Homologous to *Catharanthus roseus* and *Arabidopsis thaliana* APS Kinase

| SEQ ID NO. | Percent Identity to |
|---|---|
| 2 | 70% (gi 2832300) |
| 4 | 52% (gi 2832300) |
| 6 | 67% (gi 1076283) |
| 8 | 56% (gi 2832300) |
| 10 | 63% (gi 2832300) |
| 12 | 63% (gi 2832300) |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Sequence alignments and BLAST scores and probabilities indicate that the nucleic acid fragments comprising the instant cDNA clones encode a substantial portion of an APS kinase. These sequences represent the first corn, rice, soybean and wheat sequences encoding APS kinase.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin.

Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methyl-sulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated nucleic acid fragment comprising:
   a nucleotide sequence encoding a polypeptide having adenosine 5'-phosphosulfate kinase activity, wherein the polypeptide has an amino acid sequence consisting of SEQ ID NO:4, or
   a full-length complement of the nucleotide sequence.

2. The isolated nucleic acid fragment of claim 1, wherein the nucleotide sequence consists of SEQ ID NO:3.

3. The isolated nucleic acid fragment of claim 1, wherein the nucleic acid fragment is a functional RNA.

4. A recombinant DNA construct comprising the isolated nucleic acid fragment of claim 1 operably linked to at least one regulatory sequence.

5. A transformed host cell comprising the recombinant DNA construct of claim 4.

* * * * *

```
                         SEQUENCE LISTING

<160> NUMBER OF SEQ ID NOS: 14

<210> SEQ ID NO 1
<211> LENGTH: 890
<212> TYPE: DNA
<213> ORGANISM: Zea mays

<400> SEQUENCE: 1
ggtcagcggc ggcggccgtc gcagggatca gcagcagcag cagcgcgctg gtgacctcga      60
ccgtcgggaa atcgacgaac atcctgtggc atgagtgcgc catcgggcag aaggagcgac     120
agggtctgct gaaccagaag ggctgcgtcg tgtggatcac tggcctaagc ggttcaggga     180
aaagcacgct cgcgtgcgcg ctgagccgcg agctgcacgg cagaggccac ctcacgtacg     240
tcctcgacgg cgacaacctc aggcacgggc tgaacaggga cctcagcttc ggagcagagg     300
accgcgccga gaacatccgc agagtagggg aagtagcgaa gctgttcgcc gacgctggcc     360
tcgtctgcat cgccagcctc atatcgccct acagaagcga ccgaagcgcg tgtcgcgatc     420
tgctgcccaa gcactcgttt atcgaggtgt tcctggacgt gccgcttcaa gtgtgcgaag     480
ccagggaccc caaaggcctc tacaagctcg cacgcgccgg caaaatcaaa gggttcaccg     540
gcatcgacga tccttacgaa ccgccgtcgg actgtgagat agtgatccag tgtaaagtcg     600
gcgactgccc ttcgcctgaa tcgatggctg gtcacgttgt gtcgtacctt gagacgaatg     660
gtttcctcca ggactagaca tggaatgcga tcgatgcgtc tgatgtgtat atatgtagca     720
gcagccggag cggcattgcc aaggctgtgt aatctcatgg ctgtctttct ctttaagacc     780
aaaacaaaca agagatggca gtgtaaaaag gaaaaaaaaa actgcgtctg acagagtcgc     840
tgaatcaacc atgcttctga taaaaaaaaa aaaaaaaaaa aaaaaaaaaa                890

<210> SEQ ID NO 2
<211> LENGTH: 224
<212> TYPE: PRT
<213> ORGANISM: Zea mays

<400> SEQUENCE: 2

Ser Ala Ala Ala Ala Val Ala Gly Ile Ser Ser Ser Ser Ala Leu
  1               5                  10                  15

Val Thr Ser Thr Val Gly Lys Ser Thr Asn Ile Leu Trp His Glu Cys
                 20                  25                  30

Ala Ile Gly Gln Lys Glu Arg Gln Gly Leu Leu Asn Gln Lys Gly Cys
             35                  40                  45

Val Val Trp Ile Thr Gly Leu Ser Gly Ser Gly Lys Ser Thr Leu Ala
         50                  55                  60

Cys Ala Leu Ser Arg Glu Leu His Gly Arg Gly His Leu Thr Tyr Val
 65                  70                  75                  80

Leu Asp Gly Asp Asn Leu Arg His Gly Leu Asn Arg Asp Leu Ser Phe
                 85                  90                  95

Gly Ala Glu Asp Arg Ala Glu Asn Ile Arg Arg Val Gly Glu Val Ala
```

```
            100                 105                 110
Lys Leu Phe Ala Asp Ala Gly Leu Val Cys Ile Ala Ser Leu Ile Ser
        115                 120                 125

Pro Tyr Arg Ser Asp Arg Ser Ala Cys Arg Asp Leu Leu Pro Lys His
    130                 135                 140

Ser Phe Ile Glu Val Phe Leu Asp Val Pro Leu Gln Val Cys Glu Ala
145                 150                 155                 160

Arg Asp Pro Lys Gly Leu Tyr Lys Leu Ala Arg Ala Gly Lys Ile Lys
                165                 170                 175

Gly Phe Thr Gly Ile Asp Asp Pro Tyr Glu Pro Pro Ser Asp Cys Glu
            180                 185                 190

Ile Val Ile Gln Cys Lys Val Gly Asp Cys Pro Ser Pro Glu Ser Met
        195                 200                 205

Ala Gly His Val Val Ser Tyr Leu Glu Thr Asn Gly Phe Leu Gln Asp
    210                 215                 220
```

<210> SEQ ID NO 3
<211> LENGTH: 1217
<212> TYPE: DNA
<213> ORGANISM: Zea mays

<400> SEQUENCE: 3

| | | | | | |
|---|---|---|---|---|---|
| gcgtccgttt | catttcatca | atcaaacaga | acctctggtc | acacacacgc | agcaaccacc | 60 |
| gagcccagcg | cccggcccag | ccagccaggg | ccaacggcaa | gcaacaccc | tcctcagccc | 120 |
| gacgccgacg | ctcgccgtca | tcctcgtaaa | tccacagcgc | gcgcctcccg | tcctcccagg | 180 |
| cctcacccct | agcgatgcgc | cactcccggc | gctcgtgatc | catggcctca | ctccccgttc | 240 |
| ctcacactct | tccgcgggtc | tcgccagtga | tagtgggcgc | cgcgagggg | agggccgcgg | 300 |
| tgcgcgtacg | cactgccacc | gcggcattgg | gcggtgggtg | cggcggcggc | ggcggaatgg | 360 |
| agcagcgccc | ggggaggccc | cgcacagccc | agtgaaggag | aagcctgtaa | tgtcgaacat | 420 |
| tgggaaatcg | actaatattt | tatggcacaa | ttgcttgatt | ggacaatctg | atagacagaa | 480 |
| attgctggga | caaaaggct | gtgtcgtatg | gataacagga | ctcagtggtt | cagggaaaag | 540 |
| tactcttgca | tgtgcactga | gtcgtgagtt | gcattgcaga | ggccacctca | cgtatgtact | 600 |
| tgatggtgac | aacctcagac | atggcctaaa | tagagattta | agctttaagg | cagaagaccg | 660 |
| tgcagaaaat | atacgaagag | ttggtgaagt | ggcaaagctt | tttgctgatg | ctggtgtcat | 720 |
| atgcattgct | agcttgatat | ctccatacag | gagagatcgt | gatgcatgcc | gtgctctact | 780 |
| tccacattct | aactttattg | aagtatttat | tgatttgccc | ctaaaaattt | gtgaagctcg | 840 |
| tgatcctaaa | ggcctataca | agcttgcacg | tacaggaaag | attaaggtt | tcactggaat | 900 |
| tgatgatcca | tacgaaccac | caattaatgg | tgagatagta | attaagatga | agatgagga | 960 |
| atgcccttca | cccaaagcaa | tggccaagca | agttctatgc | taccttgaag | aaaacggata | 1020 |
| tttgcaagct | tagtatatgt | attttgagaa | gattgatctg | attcttgtgt | gtccattact | 1080 |
| tgtggacaca | ataagatctg | ttgttggtca | catgaataaa | aggcatcaac | atgtaggaag | 1140 |
| taacagaagg | tacggttcat | tcagaaacgg | atatggattc | attcgtttaa | aaaaaaaaa | 1200 |
| aaaaaaaaaa | aaaaaaa | | | | | 1217 |

<210> SEQ ID NO 4
<211> LENGTH: 343
<212> TYPE: PRT
<213> ORGANISM: Zea mays

<400> SEQUENCE: 4

```
Arg Pro Phe His Phe Ile Asn Gln Thr Glu Pro Leu Val Thr His Thr
 1               5                  10                  15

Gln Gln Pro Pro Ser Pro Ala Pro Gly Pro Ala Ser Gln Gly Gln Arg
            20                  25                  30

Gln Gly Asn Thr Leu Leu Ser Pro Thr Pro Thr Leu Ala Val Ile Leu
        35                  40                  45

Val Asn Pro Gln Arg Ala Pro Pro Val Leu Pro Gly Leu Thr Pro Ser
    50                  55                  60

Asp Ala Pro Leu Pro Ala Leu Val Ile His Gly Leu Thr Pro Arg Ser
65                  70                  75                  80

Ser His Ser Ser Ala Gly Leu Ala Ser Asp Ser Gly Arg Arg Glu Gly
                85                  90                  95

Glu Gly Arg Gly Ala Arg Thr His Cys His Arg Gly Ile Gly Arg Trp
            100                 105                 110

Val Arg Arg Arg Arg Asn Gly Ala Ala Pro Gly Glu Ala Pro His
        115                 120                 125

Ser Pro Val Lys Glu Lys Pro Val Met Ser Asn Ile Gly Lys Ser Thr
    130                 135                 140

Asn Ile Leu Trp His Asn Cys Leu Ile Gly Gln Ser Asp Arg Gln Lys
145                 150                 155                 160

Leu Leu Gly Gln Lys Gly Cys Val Val Trp Ile Thr Gly Leu Ser Gly
                165                 170                 175

Ser Gly Lys Ser Thr Leu Ala Cys Ala Leu Ser Arg Glu Leu His Cys
            180                 185                 190

Arg Gly His Leu Thr Tyr Val Leu Asp Gly Asp Asn Leu Arg His Gly
        195                 200                 205

Leu Asn Arg Asp Leu Ser Phe Lys Ala Glu Asp Arg Ala Glu Asn Ile
    210                 215                 220

Arg Arg Val Gly Glu Val Ala Lys Leu Phe Ala Asp Ala Gly Val Ile
225                 230                 235                 240

Cys Ile Ala Ser Leu Ile Ser Pro Tyr Arg Arg Asp Arg Asp Ala Cys
                245                 250                 255

Arg Ala Leu Leu Pro His Ser Asn Phe Ile Glu Val Phe Ile Asp Leu
            260                 265                 270

Pro Leu Lys Ile Cys Glu Ala Arg Asp Pro Lys Gly Leu Tyr Lys Leu
        275                 280                 285

Ala Arg Thr Gly Lys Ile Lys Gly Phe Thr Gly Ile Asp Asp Pro Tyr
    290                 295                 300

Glu Pro Pro Ile Asn Gly Glu Ile Val Ile Lys Met Lys Asp Glu Glu
305                 310                 315                 320

Cys Pro Ser Pro Lys Ala Met Ala Lys Gln Val Leu Cys Tyr Leu Glu
                325                 330                 335

Glu Asn Gly Tyr Leu Gln Ala
            340
```

<210> SEQ ID NO 5
<211> LENGTH: 431
<212> TYPE: DNA
<213> ORGANISM: Oryza sativa
<220> FEATURE:
<221> NAME/KEY: unsure
<222> LOCATION: (48)
<223> OTHER INFORMATION: n = A, C, G or T
<220> FEATURE:
<221> NAME/KEY: unsure

```
<222> LOCATION: (346)
<223> OTHER INFORMATION: n = A, C, G or T
<220> FEATURE:
<221> NAME/KEY: unsure
<222> LOCATION: (431)
<223> OTHER INFORMATION: n = A, C, G or T

<400> SEQUENCE: 5
cttacacaga gatcaggtag aacagtgggc gagaacaaag ttttgcanat gtcatcaatt      60
gtgccgaagg cgtccaatat cttctggcat gattgtgcag ttggccaggc tgatcggcag     120
aagctactga agcagaaagg ttgcgttgtt tggatcacag acttagtgg ttcaggtaaa      180 agtaccctgg catgcacatt agatcgagag ctccatacaa gagggaagct ttcttatgtt    240
cttgatggtg ataatttaag acatggtttg aacaaggatc ttggctttaa ggcggaagac    300
cgtgctgaaa atatacgcaa agttggtgag gtagcaaagc tattcncaga tgcaagccta    360
gtatgcattg caagtttcaa atctccctat aagagagaac gtgagtcctg ccctgcaat     420 attgtcaaat n                                                         431

<210> SEQ ID NO 6
<211> LENGTH: 118
<212> TYPE: PRT
<213> ORGANISM: Oryza sativa
<220> FEATURE:
<221> NAME/KEY: UNSURE
<222> LOCATION: (98)
<223> OTHER INFORMATION: Xaa = ANY AMINO ACID

<400> SEQUENCE: 6

Ser Ile Val Pro Lys Ala Ser Asn Ile Phe Trp His Asp Cys Ala Val
  1               5                  10                  15

Gly Gln Ala Asp Arg Gln Lys Leu Leu Lys Gln Lys Gly Cys Val Val
             20                  25                  30

Trp Ile Thr Gly Leu Ser Gly Ser Gly Lys Ser Thr Leu Ala Cys Thr
         35                  40                  45

Leu Asp Arg Glu Leu His Thr Arg Gly Lys Leu Ser Tyr Val Leu Asp
     50                  55                  60

Gly Asp Asn Leu Arg His Gly Leu Asn Lys Asp Leu Gly Phe Lys Ala
 65                  70                  75                  80

Glu Asp Arg Ala Glu Asn Ile Arg Lys Val Gly Glu Val Ala Lys Leu
                 85                  90                  95

Phe Xaa Asp Ala Ser Leu Val Cys Ile Ala Ser Phe Lys Ser Pro Tyr
            100                 105                 110

Lys Arg Glu Arg Glu Ser
        115

<210> SEQ ID NO 7
<211> LENGTH: 936
<212> TYPE: DNA
<213> ORGANISM: Glycine max

<400> SEQUENCE: 7
gcacgagcca ccgcgaaggc tctgcgacag ccctgctacg ccggaatctt tcgcaacatc     60
gaatgcggcc cgtcgccggc ggcggagtcg ctagggtttc cgaagctccg cggaatcaac    120
gtcactggat tgcactgcgg ccgccgaggc ctcgtcctcg tcctccgtgc aaaatcaaag    180
ccgattaggg cgaaggagaa cgcaagcgta agtgcttctc tgatcgatga ctggttcaag    240
ccaattacgg cgaaggagga ttctaacgca gaggaccgta catcttcgtt ttctggtaaa    300
```

-continued

```
aatctcaccc agatgtcaaa tgttgggaac tcgacaaaca ttatgtggca tgactgtcca    360
attcagaaac aagatagaca gcagctgctt cagcaacaag gctgtgttat atggctaact    420
ggcctcagcg atcaggaaa aagcactatt gcatgtgctc tgagtcaaag cttgcactcc    480
aaaggaaaac tgtcttacat ccttgatggt gacaatattc ggcatggtct aaaccaggat    540
cttagtttta gagcagaaga tcgttctgaa acattagaa ggattggtga ggtggcaaaa    600
ctctttgcag atgctggtgt tatttgcatc actagtttaa tatcaccata ccaaaaggat    660
agagatgcat gcagagcact actttcaaaa ggagatttta ttgaggtttt catagatgtt    720
ccactacatg tgtgtgaagc tagggaccca aagggactct acaagcttgc tcgagctgga    780
aagatcaaag gtttcactgg tatagatgat ccatatgaac caccgtgtag ttgtgagata    840
gtattacaac agaaaggaag tgactgtaag tctcccagtg atatggctga agaagtgata    900
tcctacttgg aggagaacgg atacctgcgg gcttga                             936
```

<210> SEQ ID NO 8
<211> LENGTH: 311
<212> TYPE: PRT
<213> ORGANISM: Glycine max

<400> SEQUENCE: 8

```
Ala Arg Ala Thr Ala Lys Ala Leu Arg Gln Pro Cys Tyr Ala Gly Ile
  1               5                  10                  15

Phe Arg Asn Ile Glu Cys Gly Pro Ser Pro Ala Ala Glu Ser Leu Gly
             20                  25                  30

Phe Pro Lys Leu Arg Gly Ile Asn Val Thr Gly Leu His Cys Gly Arg
         35                  40                  45

Arg Gly Leu Val Leu Val Leu Arg Ala Lys Ser Lys Pro Ile Arg Ala
     50                  55                  60

Lys Glu Asn Ala Ser Val Ser Ala Ser Leu Ile Asp Asp Trp Phe Lys
 65                  70                  75                  80

Pro Ile Thr Ala Lys Glu Asp Ser Asn Ala Glu Asp Arg Thr Ser Ser
                 85                  90                  95

Phe Ser Gly Lys Asn Leu Thr Gln Met Ser Asn Val Gly Asn Ser Thr
            100                 105                 110

Asn Ile Met Trp His Asp Cys Pro Ile Gln Lys Gln Asp Arg Gln Gln
        115                 120                 125

Leu Leu Gln Gln Gln Gly Cys Val Ile Trp Leu Thr Gly Leu Ser Gly
    130                 135                 140

Ser Gly Lys Ser Thr Ile Ala Cys Ala Leu Ser Gln Ser Leu His Ser
145                 150                 155                 160

Lys Gly Lys Leu Ser Tyr Ile Leu Asp Gly Asp Asn Ile Arg His Gly
                165                 170                 175

Leu Asn Gln Asp Leu Ser Phe Arg Ala Glu Asp Arg Ser Glu Asn Ile
            180                 185                 190

Arg Arg Ile Gly Glu Val Ala Lys Leu Phe Ala Asp Ala Gly Val Ile
        195                 200                 205

Cys Ile Thr Ser Leu Ile Ser Pro Tyr Gln Lys Asp Arg Asp Ala Cys
    210                 215                 220

Arg Ala Leu Leu Ser Lys Gly Asp Phe Ile Glu Val Phe Ile Asp Val
225                 230                 235                 240

Pro Leu His Val Cys Glu Ala Arg Asp Pro Lys Gly Leu Tyr Lys Leu
                245                 250                 255

Ala Arg Ala Gly Lys Ile Lys Gly Phe Thr Gly Ile Asp Asp Pro Tyr
```

```
            260                 265                 270
Glu Pro Pro Cys Ser Cys Glu Ile Val Leu Gln Gln Lys Gly Ser Asp
        275                 280                 285

Cys Lys Ser Pro Ser Asp Met Ala Glu Glu Val Ile Ser Tyr Leu Glu
        290                 295                 300

Glu Asn Gly Tyr Leu Arg Ala
305                 310

<210> SEQ ID NO 9
<211> LENGTH: 928
<212> TYPE: DNA
<213> ORGANISM: Triticum aestivum

<400> SEQUENCE: 9
gcacgagggc ggacgcaggg gagaggatgg cggggtcaga agccgtgccg gtggtggctg      60
tggctgccgg gaagcagccc gtcaatggat cagccatggc aggtatcgac aagcttgtga     120
cctcaactgt tgggaaatcg acaaacgttc tttggcatga ctgtccaata ggtcagtttg     180
agaggcagga actgctaaat cagaagggtt gtgttgtgtg gataacaggg ttaagtggtt     240
cagggaaaag cacactagca tgcgcgctaa gtcgcgagct gcactccaga ggtcatctga     300
cctacattct agacggtgac aatctaaggc atgggttaaa ccgagacctc tgtttcgaag     360
caaaggaccg tgctgaaaat atacgcagag taggagaagt agcaaagctg tttgcagatg     420
ctggtctgat ctgcattgct agcttgtatat caccctacag aagtgaacgc agcgcttgcc     480
gcaaattact gcacaattct acattcatcg aggtgttttt gaatgtccca cttgaagttt     540
gtgaagctag ggatccaaaa ggcttgtaca agcttgcccg tgcaggaaaa atcaaagggt     600
ttactggaat tgatgatcct tatgaagcac cttctgactg cgagatagtg atacagtgca     660
aagctggtga ctgcgccacg cctaaatcga tggctgatca agttgtgtca tatcttgaag     720
caaatgagtt cttacaggaa tagagacgta tgctatggat gaaaaaacat tctgaaattg     780
gatcgccaag ggatgtgaaa tatgaggtag tatttatgtc tagaaagagt gatgatagta     840
tgagaacata tatattgaca taaagatcga atctgtacat cattataata aattgaaatg     900
ttttgacgca aaaaaaaaaa aaaaaaaa                                        928

<210> SEQ ID NO 10
<211> LENGTH: 246
<212> TYPE: PRT
<213> ORGANISM: Triticum aestivum

<400> SEQUENCE: 10

Thr Arg Ala Asp Ala Gly Glu Arg Met Ala Gly Ser Glu Ala Val Pro
  1               5                  10                  15

Val Val Ala Val Ala Ala Gly Lys Gln Pro Val Asn Gly Ser Ala Met
                 20                  25                  30

Ala Gly Ile Asp Lys Leu Val Thr Ser Thr Val Gly Lys Ser Thr Asn
             35                  40                  45

Val Leu Trp His Asp Cys Pro Ile Gly Gln Phe Glu Arg Gln Glu Leu
 50                  55                  60

Leu Asn Gln Lys Gly Cys Val Val Trp Ile Thr Gly Leu Ser Gly Ser
 65                  70                  75                  80

Gly Lys Ser Thr Leu Ala Cys Ala Leu Ser Arg Glu Leu His Ser Arg
                 85                  90                  95

Gly His Leu Thr Tyr Ile Leu Asp Gly Asp Asn Leu Arg His Gly Leu
            100                 105                 110
```

Asn Arg Asp Leu Cys Phe Glu Ala Lys Asp Arg Ala Glu Asn Ile Arg
            115                 120                 125

Arg Val Gly Glu Val Ala Lys Leu Phe Ala Asp Ala Gly Leu Ile Cys
        130                 135                 140

Ile Ala Ser Leu Ile Ser Pro Tyr Arg Ser Glu Arg Ser Ala Cys Arg
145                 150                 155                 160

Lys Leu Leu His Asn Ser Thr Phe Ile Glu Val Phe Leu Asn Val Pro
                165                 170                 175

Leu Glu Val Cys Glu Ala Arg Asp Pro Lys Gly Leu Tyr Lys Leu Ala
            180                 185                 190

Arg Ala Gly Lys Ile Lys Gly Phe Thr Gly Ile Asp Asp Pro Tyr Glu
        195                 200                 205

Ala Pro Ser Asp Cys Glu Ile Val Ile Gln Cys Lys Ala Gly Asp Cys
    210                 215                 220

Ala Thr Pro Lys Ser Met Ala Asp Gln Val Val Ser Tyr Leu Glu Ala
225                 230                 235                 240

Asn Glu Phe Leu Gln Glu
                245

<210> SEQ ID NO 11
<211> LENGTH: 521
<212> TYPE: DNA
<213> ORGANISM: Triticum aestivum

<400> SEQUENCE: 11
gcacgaggct tgcacgcaca ggaaagatta aagggttcac cggagttgat gatccatacg    60
aatcaccagt gaatagtgag atagtaatta agatggaagg tggggaatgc ccttcaccga   120
aggcaatggc ccagcaagtt ctgtcctacc ttgagaagaa cggatatttg caggcttagc   180
atatatatac tccagatcca gaagattgaa cttattcttc tgtgtccata actcatggac   240
acaggcatga tccatttggt cgcatccgga ataaaaggcg ctgttattga agcaacaagc   300 tgccttttc acggggaaag ggacgcagat cgatgatcag tttgattgtt cggcattgct   360
cctctcgcgc gtgttgtgct attttagctg tagtctatac ttgctcattt cggctgaaat   420
ggtgtgctgt gctgtgctgt gtttatttgt tggtaatgta tgatttgatt gtgggtgtca   480
aaagtacgaa tgaataaatc gtgcttgcgt tttcaaaaaa a                       521

<210> SEQ ID NO 12
<211> LENGTH: 58
<212> TYPE: PRT
<213> ORGANISM: Triticum aestivum

<400> SEQUENCE: 12

Thr Arg Leu Ala Arg Thr Gly Lys Ile Lys Gly Phe Thr Gly Val Asp
1               5                   10                  15

Asp Pro Tyr Glu Ser Pro Val Asn Ser Glu Ile Val Ile Lys Met Glu
            20                  25                  30

Gly Gly Glu Cys Pro Ser Pro Lys Ala Met Ala Gln Gln Val Leu Ser
        35                  40                  45

Tyr Leu Glu Lys Asn Gly Tyr Leu Gln Ala
    50                  55

<210> SEQ ID NO 13
<211> LENGTH: 312
<212> TYPE: PRT
<213> ORGANISM: Catharanthus roseus

<400> SEQUENCE: 13

Met Ile Gly Ser Val Lys Arg Pro Val Val Ser Cys Val Leu Pro Glu
1               5                   10                  15

Phe Asp Phe Thr Glu Ser Thr Gly Leu Gly Lys Lys Ser Ser Ser Val
            20                  25                  30

Lys Leu Pro Val Asn Phe Gly Ala Phe Gly Ser Gly Gly Gly Glu Val
        35                  40                  45

Lys Leu Gly Phe Leu Ala Pro Ile Lys Ala Thr Glu Gly Ser Lys Thr
    50                  55                  60

Ser Ser Phe Gln Val Asn Gly Lys Val Asp Asn Phe Arg His Leu Gln
65                  70                  75                  80

Pro Ser Asp Cys Asn Ser Asn Ser Asp Ser Ser Leu Asn Asn Cys Asn
                85                  90                  95

Gly Phe Pro Gly Lys Lys Ile Leu Gln Thr Thr Val Gly Asn Ser
            100                 105                 110

Thr Asn Ile Leu Trp His Lys Cys Ala Val Glu Lys Ser Glu Arg Gln
        115                 120                 125

Glu Pro Leu Gln Gln Arg Gly Cys Val Ile Trp Ile Thr Gly Leu Ser
    130                 135                 140

Gly Ser Gly Lys Ser Thr Leu Ala Cys Ala Leu Ser Arg Gly Leu His
145                 150                 155                 160

Ala Lys Gly Lys Leu Thr Tyr Ile Leu Asp Gly Asp Asn Val Arg His
                165                 170                 175

Gly Leu Asn Ser Asp Leu Ser Phe Lys Ala Glu Asp Arg Ala Glu Asn
            180                 185                 190

Ile Arg Arg Ile Gly Glu Val Ala Lys Leu Phe Ala Asp Ala Gly Val
        195                 200                 205

Ile Cys Ile Ala Ser Leu Ile Ser Pro Tyr Arg Lys Pro Pro Asp Ala
    210                 215                 220

Cys Arg Ser Leu Leu Pro Glu Gly Asp Phe Ile Glu Val Phe Met Asp
225                 230                 235                 240

Val Pro Leu Lys Val Cys Glu Ala Arg Asp Pro Lys Gly Leu Tyr Lys
                245                 250                 255

Leu Ala Arg Ala Gly Lys Ile Lys Gly Phe Thr Gly Ile Asp Asp Pro
            260                 265                 270

Tyr Glu Pro Pro Leu Lys Ser Glu Ile Val Leu His Gln Lys Leu Gly
        275                 280                 285

Met Cys Asp Ser Pro Cys Asp Leu Ala Asp Ile Val Ile Ser Tyr Leu
    290                 295                 300

Glu Glu Asn Gly Tyr Leu Lys Ala
305                 310

<210> SEQ ID NO 14
<211> LENGTH: 276
<212> TYPE: PRT
<213> ORGANISM: Arabidopsis thaliana

<400> SEQUENCE: 14

Met Ile Ala Ala Gly Ala Lys Ser Leu Leu Gly Leu Ser Met Ala Ser
1               5                   10                  15

Pro Lys Gly Ile Phe Asp Ser Asn Ser Met Ser Asn Ser Arg Ser Val
            20                  25                  30

Val Val Val Arg Ala Cys Val Ser Met Asp Gly Ser Gln Thr Leu Ser
        35                  40                  45

```
His Asn Lys Asn Gly Ser Ile Pro Glu Val Lys Ser Ile Asn Gly His
        50                  55                  60
Thr Gly Gln Lys Gln Gly Pro Leu Ser Thr Val Gly Asn Ser Thr Asn
 65              70                  75                      80
Ile Lys Trp His Glu Cys Ser Val Glu Lys Val Asp Arg Gln Arg Leu
                85                  90                  95
Leu Asp Gln Lys Gly Cys Val Ile Trp Val Thr Gly Leu Ser Gly Ser
            100                 105                 110
Gly Lys Ser Thr Leu Ala Cys Ala Leu Asn Gln Met Leu Tyr Gln Lys
            115                 120                 125
Gly Lys Leu Cys Tyr Ile Leu Asp Gly Asp Asn Val Arg His Gly Leu
            130                 135                 140
Asn Arg Asp Leu Ser Phe Lys Ala Glu Asp Arg Ala Glu Asn Ile Arg
145                 150                 155                 160
Arg Val Gly Glu Val Ala Lys Leu Phe Ala Asp Ala Gly Ile Ile Cys
                165                 170                 175
Ile Ala Ser Leu Ile Ser Pro Tyr Arg Thr Asp Arg Asp Ala Cys Arg
            180                 185                 190
Ser Leu Leu Pro Glu Gly Asp Phe Val Glu Val Phe Met Asp Val Pro
        195                 200                 205
Leu Ser Val Cys Glu Ala Arg Asp Pro Lys Gly Leu Tyr Lys Leu Ala
        210                 215                 220
Arg Ala Gly Lys Ile Lys Gly Phe Thr Gly Ile Asp Asp Pro Tyr Glu
225                 230                 235                 240
Pro Pro Leu Asn Cys Glu Ile Ser Leu Gly Arg Glu Gly Gly Thr Ser
                245                 250                 255
Pro Ile Glu Met Ala Glu Lys Val Val Gly Tyr Leu Asp Asn Lys Gly
            260                 265                 270
Tyr Leu Gln Ala
        275
```